United States Patent [19]

Byler

[11] 4,012,129
[45] Mar. 15, 1977

[54] OPTICAL DEVICE FOR PRE-OPERATIVE CATARACT PATIENTS

[76] Inventor: William H. Byler, 690 Osceola Ave., Winter Park, Fla. 32789

[22] Filed: May 23, 1975

[21] Appl. No.: 580,318

[52] U.S. Cl. .................................. 351/46; 351/47
[51] Int. Cl.² ...................... G02C 7/16; G02C 9/04
[58] Field of Search .......................... 351/45, 46, 47

[56] References Cited

UNITED STATES PATENTS

| | | | |
|---|---|---|---|
| 1,959,915 | 5/1934 | Guthrie | 351/46 |
| 2,413,193 | 12/1946 | Robblee | 351/47 X |
| 3,171,134 | 3/1965 | Kennedy | 351/47 X |

FOREIGN PATENTS OR APPLICATIONS

| | | | |
|---|---|---|---|
| 215,766 | 1/1957 | Australia | 351/46 |

Primary Examiner—Paul A. Sacher
Attorney, Agent, or Firm—Pennie & Edmonds

[57] ABSTRACT

An optical device especially constructed for preoperative cataract patients comprising an opaque mask attached to spectacle frames or other means for mounting before the eyes. The mask includes a horizontally extending open ended slot providing a transparent area through which the patient's vision is unobstructed. The mask further includes an array of separate transparent areas disposed below the slotted opening. The size and positioning of these areas are interrelated with the slotted opening to provide an increased vertical field of vision while restricting the light striking the patient's eye to a minimum.

12 Claims, 5 Drawing Figures

OPTICAL DEVICE FOR PRE-OPERATIVE CATARACT PATIENTS

BACKGROUND OF THE INVENTION

Persons afflicted with cataracts in one or both eyes must undergo surgery to remove the cataracts. Prior to such surgery, the cataract sufferer finds that the acuity or focusing ability of his eye deteriorates over a period of time. Generally, prescription lenses are worn to provide the best acuity or focusing. However, this does not fully correct the imaging capability of the eye.

Cataracts have a light scattering effect so that light entering the eye through a wide angle is spread over the retina. This has an effect of reducing contrast of images viewed thus making such images appear blurred or out of focus. This is a particularly serious problem in higher light ambient conditions, such as on beaches and on days of bright sunshine. Also, at night, headlights of cars flood the eyes with light which affects normal eyes minimally when the eyes are directed to the road but which is scattered by cataracts and thus presents a problem to cataract patients wishing to drive at night.

To my knowledge, no optical device is presently available for pre-operative cataract patients which serves to improve vision markedly beyond that possible with prescription lenses alone while providing unrestricted field of vision horizontally and sufficient angle vertically for all practical needs. It has been proposed to produce spectacles with an array of apertures on an opaque background; for example, in U.S. Pat. No. 1,959,915. Such constructions, however, were designed for other purposes and would be unsatisfactory for use by pre-operative cataract patients who require maximum improvement of contrast while maintaining good mobility such as is needed for driving. Prior constructions such as disclosed in the cited patent admit too much light, especially from above where bright sources usually exist, while restricting horizontal vision which is critical for driving etc. Also, they fail to provide proper design for extending the field of good vision vertically which is needed for reading auto instruments, walking, etc. In fact, they tend to lead away from the unique combination of elements required by cataract patients.

SUMMARY OF THE PRESENT INVENTION

In accordance with the teachings of the present invention, one form of the optical device is comprised of an opaque mask with a centrally located and horizontally extending slotted, transparent opening. This opening extends completely across the mask to provide an unlimited horizontal field of vision. Below the slotted opening is disposed an array of transparent areas or openings. These openings function together with the slotted opening to increase the vertical field of vision. Yet, their spacing and size is held within specified limits so as to hold the increased light transmission to a minimum, while providing good vision. In this device, the aperture array is primarily a light limiting device rather than an imaging device but it must be designed so as to allow the refractive elements to function well.

The opaque mask as constructed above, may be mounted within normal spectacle frames, as, for example, where the cataract patient wears contact lenses for his prescription lenses or it may be mounted directly on prescription glasses. Alternatively, the mask may be made as a separate unit to be attached to the spectacle frame over the patient's prescription lenses as with ordinary clip-on sunglasses; or two masks may be formed as an integral structure to facilitate mounting on the spectacle frame. Still another frame type is made from suitable sheet plastic shaped to hang on spectacle frames from the back side and curved to form side pieces which provide extra protection against side entering light; the slot-aperture array film attaches easily to such surfaces. Such frames are presently available as simple sunglasses. As a base frame for the masks of the present invention, clear plastic would generally be used although tinted plastic is useful for exceptionally high ambient light conditions such as beaches.

DESCRIPTION OF THE PREFERRED EMBODIMENTS

Figure 1:
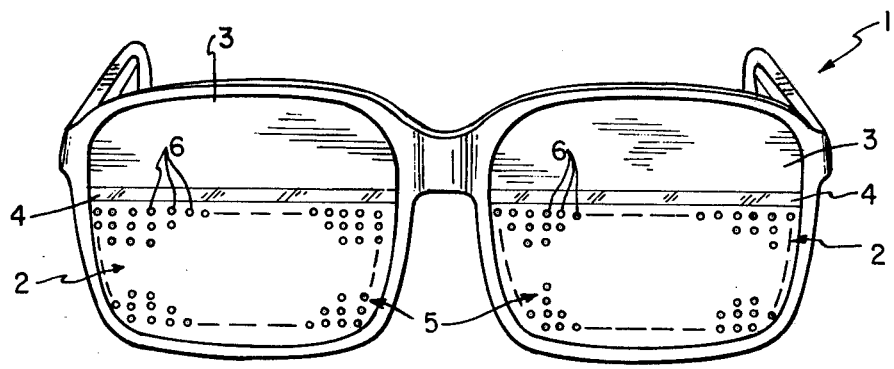
FIG. 1 is a view of a pair of eyeglass frames incorporating two of the optical devices of the present invention.

In FIG. 1 a pair of eyeglass frames 1 is shown as incorporating the optical device 2 of the present invention, one device being provided for each eye. Each optical device is fabricated from an opaque material, such as photographic film or sheet material, which can be cut into a plate mask 3 for fitting into the eyeglass frames or bonded to the lenses. In the construction shown in FIG. 1, the mask has a size which is generally square shaped.

Disposed on each opaque mask is a horizontally extending slotted transparent area or opening 4. This opening is located to be at eye level when the mask is positioned before the eye. Below this slotted opening is an array 5 of transparent areas or openings 6. Where the mask is constructed from photographic film, both the slotted opening 4 and separate openings 6 may be formed as transparent areas. Alternatively, the openings can be cut completely through the mask. As shown, the areas 6 are circular in shape this being the preferred shape; and in accordance with the teachings of the present invention, their size, spacing, overall pattern and relationship with the slotted opening is important.

As shown in FIG. 1, the slotted opening 4 extends completely across the mask. This provides an open-ended construction and permits an unlimited horizontal field of vision. This opening has a height range from 1 to 6 mm.

With respect to the transparent array 5, the individual circular transparent areas 6 have a diameter ranging from between about 0.5 to 1.2 mm. Within this range, the preferred diameter is 0.9 mm. The array pattern preferably is a parallelogram made up by the circular areas 6 disposed in about 6–20 linear rows. The center to center spacing of the transparent areas may range from about between 1.5 to 4 mm. Preferably, the spacing is between about 2–3 mm. FIG. 1 represents an embodiment having the following properties. Frame shape like ordinary clip-on sunglasses; 43 mm. height, 47 mm. width at eye level and 1570 mm.$^2$ total area; slot width 4 mm. to provide an open area of $47 \times 4 = 188$ mm.$^2$. Area below slot is 25 mm. in height giving an area of 938 mm.$^2$. This entire area is occupied by the aperture array 5 of 108 apertures of 0.9 mm. diameter spaced 3 mm. apart on centers horizontally. The top four rows are spaced vertically on 3 mm. centers while the lower five rows are spaced 2 mm. vertically. The area of each aperture is 0.636 mm.$^2$.

When viewed at an angle, the circular apertures appear as ellipses whose area decreases as the angle increases. For the mask construction of the present invention, this foreshortening effect makes the overall array 0.66 as transparent as when viewed normal to its surface. The percentage reduction in transparency is called the foreshortening factor. Closer vertical spacing helps reduce the foreshortening effect while larger apertures at the bottom would achieve a similar result.

By calculating transparencies or transmissions of the openings in relation to total areas; the array transmission per se for specification purposes can be obtained:

Array transmission
(normal to surface) $= \frac{108 \times 0.636}{938} = 7.34\%$ Array transmission
(effective) $= 7.34 \times 0.66 = 4.85\%$ Slot transmission $= \frac{188}{1570} = 12\%$ Overall transmission
(normal) $= \frac{188 + (108 \times 0.636)}{1570} = 16.4\%$ Overall transmission
(effective) $= \frac{188 + (108 \times 0.636 \times 0.66)}{1570} = 14.9\%$ It is meaningful to make these calculations in terms of overall lens area because scattering of light by the cataract is the concern and light entering through a wide angle contributes to the degradation of contrast.

It will be seen, therefore, that the aperture array adds only 2.9% to the 12% slot transmission while increasing the vertical field from about 22° to about 78°. For comparison, a slit width increase of 1 mm. would increase transmission 3 percent; $0.12 \times 5/4 - 0.12 = 0.03$ while increasing the vertical field by only about 6°.

The normal array transmission of the construction described above is 7.34 percent and this falls within the preferred range of about 2.5 to 10 percent.

Figure 2:
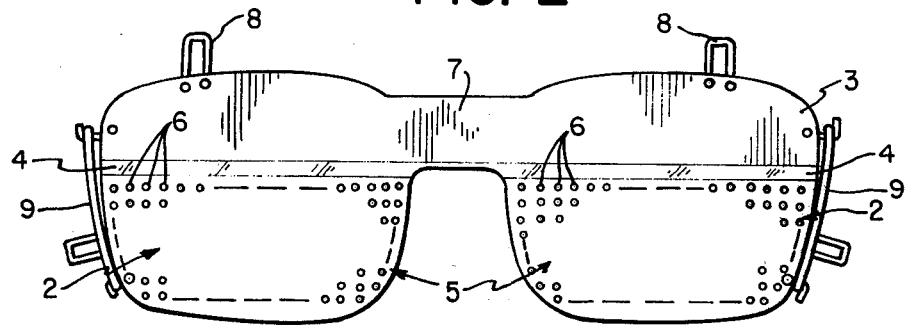
FIG. 2 is a view of a modified embodiment of the optical device of the present invention.

Although the above calculations have been made with respect to the embodiment shown in FIG. 1, the individual construction of the optical device, as far as the effective viewing surface of the mask is concerned, may be identical in the construction shown in FIG. 2. The construction of FIG. 2 differs mainly from that in FIG. 1 in that it is designed as a clip-on device to be placed over the conventional prescription glasses worn by the cataract patient.

In the embodiment of FIG. 2, the optical device is preferably formed of thin opaque material such as photographic film or opaque plastic with the transparent slotted opening 4 and areas 6 being produced photographically or by other suitable means. In order to maintain the slotted openings of each mask aligned with each other and in a horizontal plane when attached to the eyeglass frame, the two masks are integrally connected by a bridging portion 7. This bridging portion will align with the bridging portion of the conventional eyeglass frame. In adition to the integrally formed masks of FIG. 2, a pair of masks may be provided on a conventional type clip-on frame. Frames of this type are readily available on the market and are used primarily as sunglasses. The two masks would be connected together across the bridge by a flexible metal strip. The clip-on type of construction would be provided with suitable bendable clips for attaching to conventional eyeglass frames.

Figure 3:
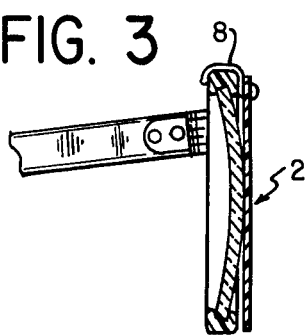
FIG. 3 is a cross-sectional view showing the embodiment of the optical device of FIG. 2 as mounted on a conventional pair of prescription eyeglasses.

The actual attachment of the embodiment of the optical device shown in FIG. 2 to the eyeglass frame is also accomplished by means of the bendable clips 8. As shown in FIG. 3, these clips can be bent around the top of the conventional eyeglass frame. By using clips of extended length, they may be bent at any location intermediate their length. This facilitates vertical adjustment of the optical device on the eyeglass frame. The top clips 8 are connected directly to the optical device. The side clips, however, are connected by resilient bands 9 to the optical device. This permits easy attachment of the device to conventional eyeglass frames. The top bent clips are simply placed over the eyeglass frames; and the bent side clips are then simply pulled outwardly against the force of the elastic bands and engage on the sides of the eyeglass frame.

Figure 4:
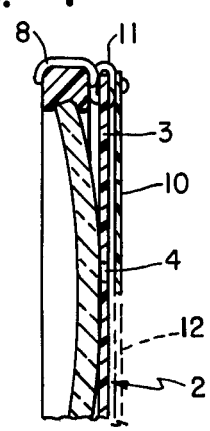
FIG. 4 is a cross-sectional view similar to FIG. 3 showing the inclusion of a light reducing shield.

FIG. 4 shows a further embodiment of the optical device of the present invention wherein light transmission is further reduced without reducing the field of vision. In this embodiment, a tinted shield 10 is attached to each mask along the top thereof. For this purpose, bendable clips 11 are provided. The shield 10 extends down along the mask to cover the slotted opening 4. Alternatively, the tinted shield may extend below the slotted opening 4 and across the aperture array 5. This construction is shown in dotted lines at 12. It thus functions similar to sunglasses. In the preferred construction, the tinting of the shield is such so as to reduce the transmission of light to about 15-30 percent. The shield in the embodiment of FIG. 4 is particularly suitable for use in areas of bright light. Addition of a 20 percent transmission sunglass or tinted plastic over the slot reduces overall transmission from 14.9 percent to only 5.3 percent. Thus, there is a radical reduction of light reaching the eye while normal sunglass transmission is retained through the slot. By extending the tint over the array as well as the slot, overall transmission goes down to about 3 percent which is far lower than any available sunglasses.

Going still lower by reducing slot width to 1 mm. and with 20 percent tint overall, transmission is about 1.2 percent. This is found to be acceptable under very bright conditions such as on a beach since mobility is still good. The present invention provides a wide range of choices to suit a variety of conditions and it is relatively simple to make adjustments to suit the individual's needs. For example, either half or full sunglasses or tinted plastic can be attached; and slit width can be changed either by a mechanical means or by simply attaching a tape over a portion of the slit. The hang-on type of frame described above is so inexpensive that it is feasible to carry more than one with varied patterns for different conditions.

Figure 5:
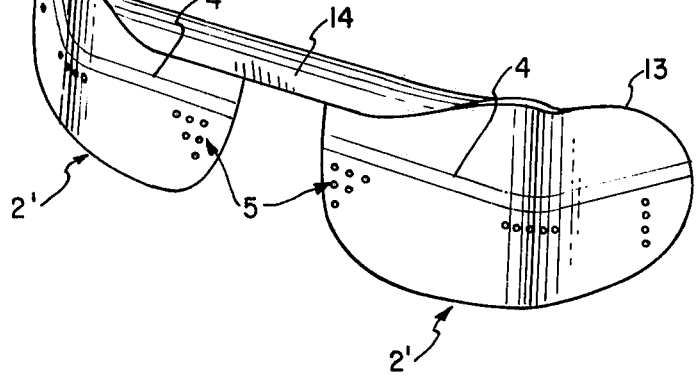
FIG. 5 is a view of another modified embodiment of the optical device of the present invention.

A further embodiment of the present invention is shown in FIG. 5. Here, a pair of optical devices 2' having a wrap around configuration are provided. As with the masks of the embodiments of FIGS. 1 and 2, a horizontal slotted opening 4 is provided at eye level with an array 5 of transparent areas or openings below the opening 4. This embodiment can be formed from a conventional plastic sunglass shield as shown in FIG. 5 to provide the wrap around effect. The wrap around of the masks extends the masks laterally beyond the eyes. The side sections which are designated at 13 in FIG. 5 extend laterally and backwardly of the individual's eyes until engagement with the face. These sections thus provide physical protection and extend the operative areas of the masks.

The device shown in FIG. 5 has a top section 14 which is curved forwardly and downwardly. This curved section provides means for hanging the device onto conventional eyeglass frames.

In addition to being helpful to cataract patients, the devices of the present invention are useful to many others who are sensitive to bright light. Even if extremely dense sunglasses were available, they would not serve as well. This unique combination of specific openings or transparent areas in an otherwise opaque mask offers performance which is not possible with a uniform density sunglass. The lower limit of the slot width of 1 mm. provides a significant advantage in giving approximately 6° vertical angle of vision. Further decrease, however, entails significant visual sacrifice without decreasing overall transmission significantly.

I claim:

1. An optical device in combination with means for holding the device in position before the eye, said optical device including:
    a. an opaque mask for mounting before the eye;
    b. a horizontal slotted opening extending completely across said mask centrally thereof, said opening having a height of about 1 to 6 mm.;
    c. an array of discrete circular transparent areas on said mask, said areas being disposed below said slotted opening and each having equal diameters of between about 0.5 and 1.2 mm. and located on centers spaced equally from each other from between about 1.5 to 4 mm.;
    d. said transparent areas providing light transmission in direction normal to the surface of between about 3 and 10 percent of the light striking the total area of the mask covered by said array; and
    e. said mask being opaque above the slotted opening.

2. The optical device according to claim 1 wherein:
    a. said array of transparent areas is defined by circular areas disposed below said slotted opening in about 6–20 linear rows and with vertical center to center spacing of the top rows being about 3 mm. and that of the bottom rows being about 2 mm.

3. The optical device according to claim 1 wherein:
    a. the vertical height of said slotted opening is constructed to provide between about 5° and 35° vertical field of vision when the mask is positioned before the eye.

4. The optical device according to claim 1 wherein:
    a. the vertical height of said slotted opening is about 4 mm.; and
    b. the diameter of each of the transparent areas is about 0.9 mm.

5. The optical device according to claim 1 wherein:
    a. the mask has a front section for disposition in front of the individual's eyes; and
    b. side sections extending from the front sections in a generally curved pattern for disposition to the side of the individual's eyes.

6. The optical device according to claim 5 further including:
    a. two opaque masks of identical construction integrally connected together along the front top edges; and
    b. an outwardly and downwardly curved section along the top edge for hanging onto the frames of conventional eyeglasses to position the optical device before the individual's eyes.

7. The optical device according to claim 1 wherein:
    a. said slotted opening is color tinted to reduce the transmission of light therethrough.

8. The optical device according to claim 7 wherein:
    a. the array of discrete transparent areas below the slotted opening are color tinted.

9. The optical device according to claim 7 wherein:
    a. the color tinting has a density which reduced light transmission to about 15 to 30 percent.

10. The optical device according to claim 9 wherein:
    a. the mask has a total area of about 1570 mm.$^2$ and the slotted opening and transparent areas provide light transmission of about 15 percent of the light striking the mask.

11. The optical device according to claim 1 including:
    a. two opaque masks of identical constructions integrally connected together along their top edges; and
    b. bendable clip means fixed to the masks for attachment of the optical device to the frame of a conventional pair of eyeglasses.

12. The optical device according to claim 11 further including:
    a. elastic means attached to the sides of the opaque masks for mounting two of the clips used for attaching the optical device to the frame of a conventional pair of eyeglasses.

* * * * *